United States Patent
Kantonen et al.

(10) Patent No.: US 7,020,238 B1
(45) Date of Patent: Mar. 28, 2006

(54) ADAPTER AND ANALYZER DEVICE FOR PERFORMING X-RAY FLUORESCENCE ANALYSIS ON HOT SURFACES

(75) Inventors: Esko Juhani Kantonen, Helsinki (FI); Janne Adolf Petteri Kesälä, Espoo (FI); Erkki Tapani Puusaari, Espoo (FI); Heikki Johannes Sipilä, Espoo (FI)

(73) Assignee: Oxford Instruments Analytical Oy, Espoo (FI)

( * ) Notice: Subject to any disclaimer, the term of this patent is extended or adjusted under 35 U.S.C. 154(b) by 0 days.

(21) Appl. No.: 11/047,247

(22) Filed: Jan. 31, 2005

(51) Int. Cl.
*G01N 23/223* (2006.01)

(52) U.S. Cl. ............... 378/44; 378/45; 378/102; 378/161

(58) Field of Classification Search .......... 378/44, 378/45, 46, 50, 160, 161; 250/492.3, 493.1, 250/390.11; 422/22
See application file for complete search history.

(56) References Cited

U.S. PATENT DOCUMENTS

| | | | | |
|---|---|---|---|---|
| 4,429,409 A | * | 1/1984 | Berry et al. | 378/45 |
| 5,075,555 A | * | 12/1991 | Woldseth et al. | 250/370.15 |
| 5,561,294 A | * | 10/1996 | Iddan | 250/330 |
| 6,178,227 B1 | * | 1/2001 | Sato | 378/117 |
| 6,765,986 B1 | * | 7/2004 | Grodzins et al. | 378/46 |

OTHER PUBLICATIONS

"The New Standard in Portable Analysis Instrumentation," Niton Product Brochure For XLi 800 and Xlt 800, Apr. 2002.*

"The World Standard in Portable XRF Spectroscopy," Product Brochure for Niton Analyzers, 2004.*

"Portable Alloy Analysis: Charting a New Course to the Future," Niton Product Brochure For XLi 800 and Xlt 800, Apr. 2002.*

* cited by examiner

*Primary Examiner*—Edward L. Glick
*Assistant Examiner*—Irakli Kiknadze
(74) *Attorney, Agent, or Firm*—Wood, Phillips, Katz, Clark & Mortimer

(57) ABSTRACT

The measurement head (101) of an X-ray fluorescence analyzer device is protected against heat from a hot target by using an adapter (201). It comprises a sheet of material having low thermal conductivity and has a three-dimensional shape that follows the form of a front part of the measurement head (101). Said sheet of material is attached to said measurement head (101) and has a central part (401) which defines an opening (202) coincident with a radiation window (109) in said measurement head (101). Said attachment means (204, 205, 301, 302, 311, 312) are located at a part of said sheet of material that is distant from said central part (401).

18 Claims, 2 Drawing Sheets

ADAPTER AND ANALYZER DEVICE FOR PERFORMING X-RAY FLUORESCENCE ANALYSIS ON HOT SURFACES

TECHNICAL FIELD

The invention concerns generally the technology of performing X-ray fluorescence analysis of objects using a portable analyzer device. Especially the invention concerns protecting the analyzer device and potentially also its user against excess heat when the object to be analyzed is hot.

BACKGROUND OF THE INVENTION

X-ray fluorescence analysis is a general designation of all techniques based on irradiating a target with X-rays, collecting fluorescent radiation induced in said target by said X-rays and drawing conclusions about the characteristics of said target on the basis of the intensity and frequency spectrum of the fluorescent radiation. Common applications of X-ray fluorescence analysis include investigating the material composition of the target. In many cases the main interest is to determine, how much the target contains some additive, pollutant or other minority constituent that can have important, potentially harmful effects, such as sulphur in liquid fuels or lead in paints. In other cases the analysis aims simply at determining the relative amounts of the main constituent materials, such as the different metals included in an alloy.

FIG. 1 is a schematic, partly cut-out diagram of a typical portable X-ray fluorescence analyzer device. Main parts thereof are a handheld measurement head 101 and a portable support unit 102 acting as a power source as well as a data processing and storage unit. If the processing and storage electronics can be made small enough, the whole analyzer device may even consist solely of the measurement head 101. The measurement head 101 comprises a handle 103 and a component compartment 104, which houses an X-ray source 105 and a detector 106. In order to suppress temperature-dependent interference there is a cooling arrangement 107 adapted to actively cool the detector 106. The cooling arrangement 107 includes typically a peltier element or a corresponding thermoelectric cooling device.

In order to perform an X-ray fluorescence analysis of a target, a front end 108 of the measurement head is pressed against a surface of the target. The X-ray source 105 emits incident X-rays towards the target through a window 109 located at the front end 108. The part of the window 109 that is transparent to incident X-rays and fluorescence radiation is typically made of (Kapton) polymide film or the like. Fluorescent X-rays that originate in the irradiated target enter the measurement head 101 through the window 109 and hit the detector 106.

If the surface of the target is hot, pressing the front end 108 against it will cause heat to be transferred to the body of the measurement head 101, which in turn gradually increases the internal temperature of the measurement head 101. The cooling arrangement 107 is only capable of maintaining some maximum temperature difference $\Delta T_{max}$ between the detector 106 and its surroundings. If the ambient temperature increases beyond a certain threshold, not even a maximum effort made by the cooling arrangement 107 will be sufficient to keep the detector 106 from reaching a cut-off temperature at which it will not be able to provide reliable results any more. The analyzer device typically includes a monitoring function, which will shut it off or at least produce an alarm if the temperature of the detector is not within some predetermined limits.

An obvious solution for improving the usability of an analyzer device for measuring hot surfaces would be to use a more effective cooling arrangement, and/or to extend its area of influence so that it will also cool the outer cover and other structural parts of the measurement head. However, such an obvious solution is unattractive especially from the viewpoint of power management. Thermoelectric cooling has relatively low efficiency (at least concerning the implementations known at the time of writing this description), which means that it draws a relatively high amount of electric power. In a portable analyzer device electric power comes from (rechargeable) batteries, so increasing power consumption will inevitably shorten battery life and thus decrease usability. Another obvious solution would be to make the outer cover of the measurement head from a material that has low thermal conductivity. However, the outer cover is there also for other purposes than for temperature shielding, and these other purposes may place other requirements to the material that are even contradictory to low thermal conductivity or at least require making compromises.

Yet another obvious solution would be not to press the end of the measurement head against the hot surface at all, but to keep it close to it at a small distance. This, however, involves at least two serious drawbacks. The measurement geometry will not be the same as in a press-against measurement, which will introduce a systematic error to the results. Additionally some X-ray radiation might escape into unwanted directions, which causes a small but not insignificant radiation hazard if the user of the device is not careful. Typically the front end of a measurement head includes a proximity sensor that prevents incident X-rays from being switched on if the front end is not pressed firmly against a surface of a target to be measured.

SUMMARY OF THE INVENTION

An objective of the present invention is to provide temperature protection to an X-ray fluorescence analyzer device. This objective should be achieved in a way that is advantageous from manufacturing point of view and cost-effective, and places little restrictions to the other viewpoints that must be considered in designing the device.

The objectives of the invention are achieved by providing an adapter that essentially covers the front end of the measurement head except for the necessary windows for the radiation to pass through, leaves an air gap between it and the surface of the measurement head and is attached thereto with attachment means that have low thermal conductivity.

An adapter according to the invention is characterized in that it comprises a sheet of material having low thermal conductivity and a three-dimensional shape that follows the form of a front part of a measurement head of the X-ray fluorescence analyzer device, and attachment means for attaching said sheet of material to said measurement head, said sheet of material having a central part which defines an opening which is adapted to coincide with a window in said measurement head when said sheet of material is attached to said measurement head through said attachment means, and said attachment means being located at a part of said sheet of material that is distant from said central part.

The invention applies also to an analyzer device, which is characterized in that it comprises:

a measurement head having a window in a front end of said measurement head for excitation X-rays and fluorescent radiation to pass through, and attached to said measurement head a sheet of material having low thermal conductivity and a three-dimensional shape that follows the form of said measurement head around said front end;

wherein a central part of said sheet of material defines an opening which is coincident with said window in said measurement head, and the attachment between said sheet of material and said measurement head is accomplished through attachment means located at a part of said sheet of material that is distant from said central part.

According to the invention, an adapter is placed between the front end of a measurement head and the surface of the target to be measured. For convenience it is most advantageous to have the adapter at least semipermanently fixed to the measurement head, so that it does not need to be handled separately. The adapter defines an auxiliary surface, which is to be pressed against the target to be analysed. Behind this auxiliary surface there is most advantageously a thermally insulating layer, such as an air gap or a layer of a thermally insulating solid material, which separates the adapter from the front end of the measurement head. Also the material of the adapter proper has most advantageously as low thermal conductivity as possible, taken account however that it must stand high temperatures and also be mechanically durable. A hole or window in the adapter allows incident X-rays and fluorescent radiation to pass through.

Beyond the part that defines said auxiliary surface it is usually most advantageous to make the adapter conform to the form of the outer surface of the measurement head. One advantage gained therethrough is sleek appearance: the adapter does not change much the overall outer appearance of the measurement head, and does not constitute protrusions that might make the device too bulky for field use. Another advantage is that the mechanical attachment of the adapter to the measurement head can be accomplished at a location relatively far from the part that will be in contact with the hot target surface, which lengthens the thermal bridge between the target and the body of the measurement head and consequently slows down the conduction of heat.

It is possible, however, to extend the adapter so that it will shield the user, or at least his hand, from heat radiated by the target. The same shielding function might also help to increase protection against scattered incident X-rays.

The exemplary embodiments of the invention presented in this patent application are not to be interpreted to pose limitations to the applicability of the appended claims. The verb "to comprise" is used in this patent application as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE INVENTION

Figure 1:
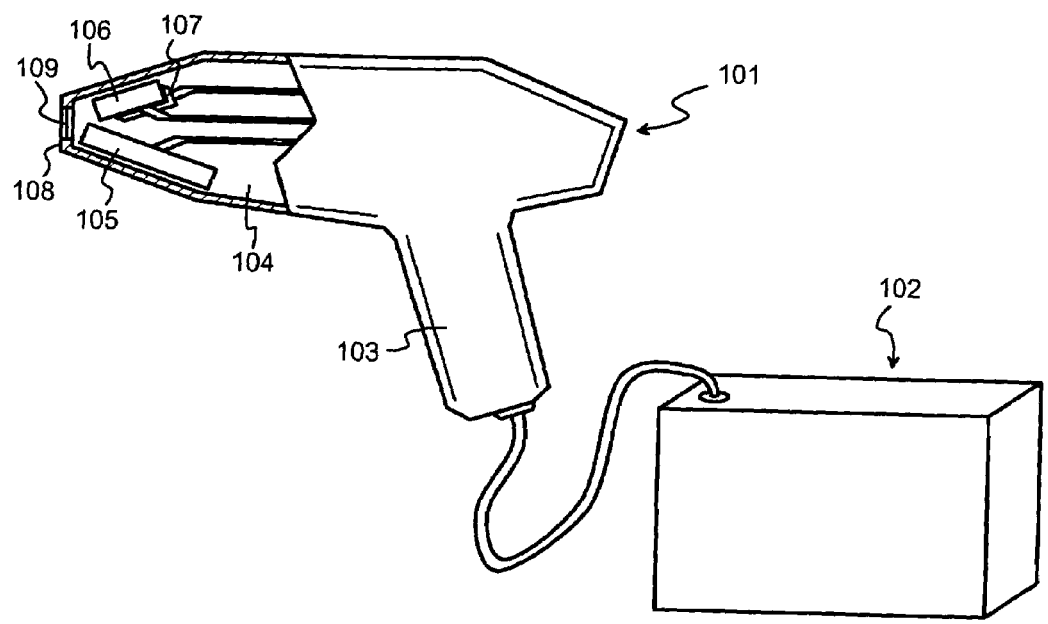
FIG. 1 illustrates a prior art X-ray fluorescence analyzer device.
Figure 2:
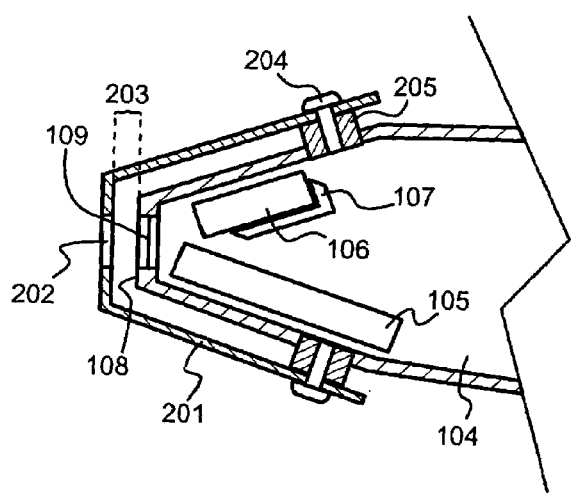
FIG. 2 illustrates an adapter according to an embodiment of the invention.

FIG. 2 is a partial cut-out diagram of a part of a portable X-ray fluorescence analyzer device equipped with an adapter according to an embodiment of the invention. The front part of the component compartment 104, as well as the X-ray source 105, detector 106 and cooling arrangement 107 are visible in the drawing. Supported in front of the front end 108 is an adapter 201, which is basically a sheet of material having certain advantageous qualities such as low thermal conductivity, bent to a three-dimensional shape in which is roughly follows the form of those parts of the analyzer device it covers. A hole 202 in the adapter coincides with the window 109 in the front end 108 of the analyzer device. A thermally insulating layer, which in the embodiment of FIG. 2 is an air gap 203 but which could also be a layer of a thermally insulating solid material, separates the adapter 201 from the front end 108 of the measurement head. In this exemplary embodiment the thickness of said thermally insulating layer (i.e. the air gap 203) is approximately 1 mm. In order not to cause excessive changes in measurement geometry it is advantageous to aim at a relatively small total thickness of anything that comes between the front end 108 and the target to be measured.

Figure 3A:
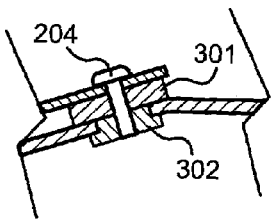
FIGS. 3a and 3b illustrate alternative details of an adapter otherwise similar to that of FIG. 2.
Figure 3B:
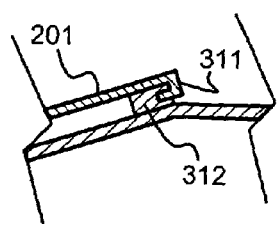

In the embodiment of FIG. 2 the adapter 201 is attached to the measurement head with screws 204, each of which engages with a corresponding thermally insulating bushing 205 attached to the outer cover of the measurement head. In this embodiment the bushings 205 extend slightly outwards from the outer surface of the measurement head, which automatically causes the adapter 201 to take a position separated by a small distance from the outer surface of the measurement head. FIGS. 3a and 3b illustrate some alternative embodiments: in FIG. 3a a thermally insulating washer 301 is placed between the adapter 201 and the outer surface of the measurement head, and the screw 204 extends through said washer 301 to a (preferably thermally insulating) nut or bushing 302 that locks itself into a hole in the outer cover of the measurement head. In FIG. 3b a bent edge 311 of the adapter 201 engages with a corresponding groove in a thermally insulating attachment block 312 attached to the outer cover of the measurement head. Said groove could also be an integral form of the outer cover proper.

For the purposes of the invention the exact nature of the attachment between the adapter and the measurement head is not important. However, it should fulfil certain criteria of advantageousness. For example, the physical attachment that inevitably constitutes a thermal bridge between the two pieces should be located as far as reasonably possible from those parts of the adapter that will touch the hot target surface. The attachment should also be rigid enough to keep the geometry of the combined structure essentially constant, taken into account a typical force with which a user will press the measurement head against a target. In order to enable easy maintenance and replacement, the attachment should be of detachable; however, permanently fixed attachments such as sealing with a chemical compound are not excluded, especially if they help to maintain a vacuum that might constitute a part of the thermal insulation between the adapter and the measurement head in some embodiments of the invention.

The material and surface characteristics of the adapter 201 should be carefully considered. One very advantageous material is stainless steel. It has relatively low thermal conductivity compared to many other metals, it has excellent mechanical and chemical durability, it is readily available in thin sheets, it requires no specific tools or techniques for processing, and it lends itself easily to various surface treatments that can be used to enhance its thermal characteristics. Other suitable materials include but are not limited to various ceramic materials, some high temperature plastics as well as ceramic matrix composites (CMCs). If the adapter 201 is made of stainless steel, a sheet thickness less than 1 mm should be sufficient.

Those surfaces of the adapter 201 that will face the hot target should be treated to achieve low absorption of infrared (heat) radiation at wavelengths that will be of importance in the radiation spectrum of a target with a surface temperature close to 400 degrees centigrade. In a stainless steel adapter this is usually achieved most easily by polishing the outer surface of the adapter. The inner surface of the adapter should have as low thermal emissivity as possible at wavelengths between room temperature and 400 degrees centigrade. For a person skilled in the art various known ways of treating the adapter surfaces are available for experimentation, in order to find the most suitable surface treatments.

It should be noted that the blackbody emissivity and absorptivity of a surface are physically closely bound to each other. It is possible to produce a surface that has low absorptivity towards shorter wavelengths (high temperatures) and high emissivity towards longer wavelengths (low temperatures). By using such a surface as the outer surface of an adapter according to an embodiment of the invention we may produce an adapter that in respect of its radiation budget tends to cool down even in conditions where it is exposed to considerable amounts of high-temperature dominated infrared radiation. However, X-ray fluorescence measurements are usually carried out in normal atmospheric conditions, where also the convection of air has a significant effect to the temperatures of the various physical pieces involved, which should not be neglected in selecting the surface properties of the adapter.

Figure 4:
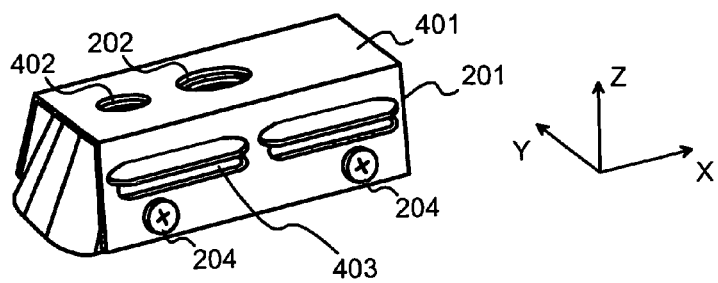
FIG. 4 illustrates an adapter according to an embodiment of the invention.

FIG. 4 is a perspective illustration of an adapter 201 according to an embodiment of the invention, attached with screws 204 to a measurement head, only the very front part of which is visible in the drawing. We assume that, according to common design practice at the time of writing this description, the "nozzle" or front part of the measurement head is somewhat elongated in one direction (direction X in FIG. 4) and much narrower in the perpendicular direction (direction Y in FIG. 4), said directions being perpendicular to the nominal propagation direction of the excitation radiation (direction Z in FIG. 4). The main design of the adapter 201 follows this form, so that the front side 401 of the adapter is elongated in the X direction and much narrower in the Y direction, and not any larger than what is needed to essentially cover the front end of the measurement head. The front side 401 is the side to be pressed against the target to be measured, so keeping it relatively small enables performing measurements even when there is not much space or when the surface of the target is not even. Additionally a small front side 401 means a small heat exchanging surface, which helps to reduce the amount of thermal energy transferred from the target to the measurement head.

The front side 401 may comprise also other formations than the hole 202 meant for the radiation to pass through. As an example, FIG. 4 illustrates a hole 402 for the proximity sensor. In order to lengthen the path of thermal conduction between the front side 401 and the attachment points at which a thermal bridge is formed to the body of the measurement head, it is possible to use holes and other kinds of forms in the sides of the adapter. FIG. 4 illustrates an example, in which two wide U-shaped cuts 403 have been made to the side of the adapter, and the flaps thus defined have been bent slightly outwards to keep infrared radiation from entering inside the adapter through the holes.

Figure 5:
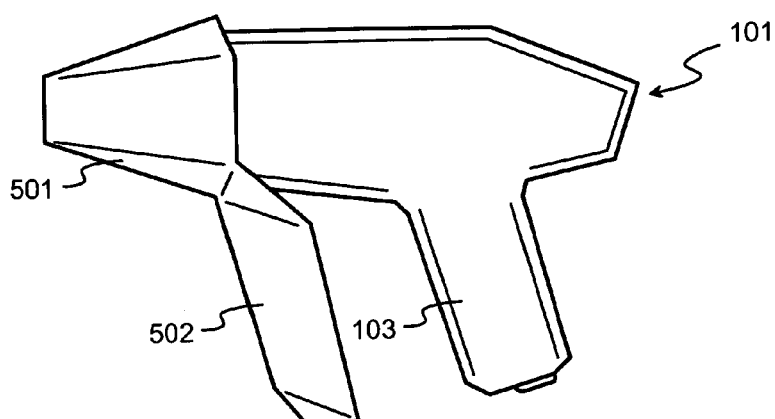
FIG. 5 illustrates an adapter according to another embodiment of the invention and FIG. 6 illustrates functional blocks of an analyzer device according to an embodiment of the invention.

Even if a relatively small adapter that follows closely the form of the front part of the measurement head is most convenient in not introducing any additional clumsiness, in some cases it may become advantageous to use a larger adapter. FIG. 5 illustrates a case in which a measurement head 101 is equipped with an adapter that, in addition to a front part 501 that as such would resemble the small adapter 201 described above, comprises an extension part 502 which in the measurement position extends between the target and the handle 103 of the measurement head. The main purpose of the extension part 502 is to protect the user's hand from infrared radiation coming from the hot target. Additionally if the stopping power of the adapter material is high enough, the extension part 502 protects the user's hand from any scattered X-rays that might come from the target material past the other parts of the measurement head.

Any extension parts or widened hems of the adapter might be flexible, collapsible and/or detachable in order to provide additional convenience of use. An extension part ot widened hem of the adapter might also extend essentially symmetrically to all directions around the front end, in order to provide protection in all directions against infrared and other radiation coming from the target.

Figure 6:
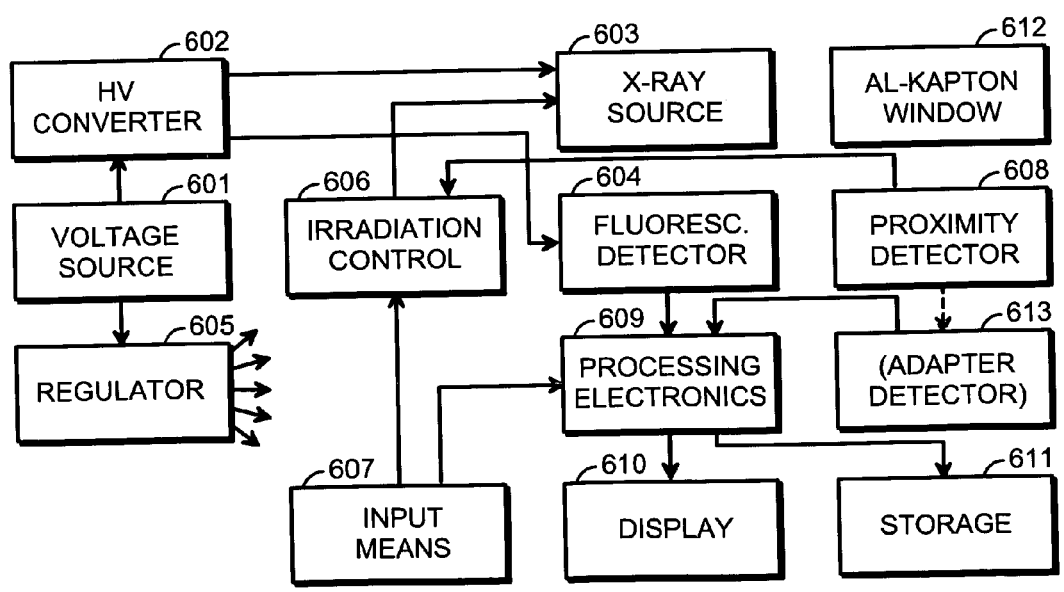

FIG. 6 illustrates some functional blocks and parts of an X-ray fluorescence analyzer device according to an embodiment of the invention. A voltage source provides operating voltages through a high voltage converter 602 to the X-ray source 603 and fluorescence detector 604, and through a regulator 605 to all parts that need low-level operating voltages. The operation of the X-ray source 603 is controlled by an irradiation control unit 606, which receives inputs from input means 607 available for a user as well as from a proximity detector 608. A processing electronics block 609 is adapted to receive inputs from the fluorescence detector 604 and from said input means 607, to process the measurement results and to provide processed information to a display 610 and storage means 611.

As a part of the thermal shielding the analyzer device comprises an aluminized kapton window 612 for the excitation X-rays and fluorescent radiation to pass through. The aluminization of the window is thin enough not to cause any significant attenuation of the excitation X-rays or fluorescent radiation, but reflects infrared radiation and thus blocks heat radiated by the target from entering directly the measurement head. Also other IR-reflective materials than aluminum may be used to produce an IR-reflective coating on the window, and also other materials than kapton can be used as the base material thereof.

Using an adapter between the front end of the measurement head and the target will change the measurement geometry, which must be taken into account in the operation of the processing electronics block 609. Several possibilities exist. According to a very simple alternative, the adapter is small and compact enough to be kept in place constantly (it has been noted that the additional sinking provided by the adapter and the air gap help significantly to protect the kapton film window) an the processing electronics block 609 has simply been programmed to always make its calculations in a measurement geometry that takes the adapter into account. According to another alternative the user is expected to give an "adapter in place" input command through the input means 607 when the adapter is in use, and the processing electronics block 609 is adapted to take such an input command into account by switching to a calculational model that takes the adapter into account.

According to yet another alternative the analyzer device comprises a separate adapter detector 613, which is adapted to automatically give an "adapter in place" signal to the processing electronics block 609, which is then adapted to take this signal into account in the same way as was described above concerning a manually inputted command. As a modification of this alternative the adapter detector 613 may be implements in connection with the proximity detector 608, or even completely replaced with a multifunctional proximity detector, so that when the proximity detector detects a target being very close to but not in direct contact with the front end of the measurement head, it informs the processing electronics block 609 that an adapter must be in use.

We claim:

1. An adapter for protecting a measurement head of an X-ray fluorescence analyzer device against heat from a hot target, comprising a sheet of material having low thermal conductivity and a three-dimensional shape that follows the form of a front part of a measurement head of the X-ray fluorescence analyzer device, and attachment means for attaching said sheet of material to said measurement head, said sheet of material having a central part which defines an opening which is adapted to coincide with a window in said measurement head when said sheet of material is attached to said measurement head through said attachment means, and said attachment means being located at a part of said sheet of material that is distant from said central part.

2. An adapter according to claim 1, wherein said sheet of material is made of stainless steel.

3. An adapter according to claim 1, wherein said sheet of material is made of a material selected from a group consisting of: ceramic, high-temperature plastic, ceramic matrix composite.

4. An adapter according to claim 1, wherein said attachment means comprise screws and bushings made of thermally insulating material, said bushings being adapted to lock into holes in an outer cover of said measurement head.

5. An adapter according to claim 4, wherein said attachment means additionally comprise, coincident with each screw, a thermally insulating washer between said sheet of material and said outer cover of said measurement head.

6. An adapter according to claim 1, wherein said three-dimensional shape of said sheet of material comprises a front side and two sides, and said attachment means are located at edges of said two sides distant from said front side.

7. An adapter according to claim 6, additionally comprising at least one opening in at least one of said two sides between said front side and said attachment means.

8. An adapter according to claim 1, wherein the surface of said sheet of material comprises a surface treatment resulting in low absorptivity of thermal radiation emitted by target surfaces having temperatures of 400 degrees centigrade.

9. An adapter according to claim 1, additionally comprising an extension part adapted to extend between a target surface to be measured and a handle of said measurement head when said sheet of material is attached to said measurement head through said attachment means.

10. An X-ray fluorescence analyzer device for irradiating a target with excitation X-rays and detecting fluorescent radiation induced in the target, comprising:
   a measurement head having a window in a front end of said measurement head for excitation X-rays and fluorescent radiation to pass through, and
   attached to said measurement head a sheet of material having low thermal conductivity and a three-dimensional shape that follows the form of said measurement head around said front end;
wherein a central part of said sheet of material defines an opening which is coincident with said window in said measurement head, and the attachment between said sheet of material and said measurement head is accomplished through attachment means located at a part of said sheet of material that is distant from said central part.

11. An X-ray fluorescence analyzer device according to claim 10, comprising a thermally insulating layer between said sheet of material and said front end of said measurement head.

12. An X-ray fluorescence analyzer device according to claim 11, wherein said thermally insulating layer is an air gap.

13. An X-ray fluorescence analyzer device according to claim 11, wherein said thermally insulating layer is a layer of a thermally insulating solid material.

14. An X-ray fluorescence analyzer device according to claim 10, wherein said window comprises a polymer film coated with an infrared-reflective coating.

15. An X-ray fluorescence analyzer device according to claim 14, wherein said polymer is a polymide film and said infrared-reflective coating is a layer of aluminum.

16. An X-ray fluorescence analyzer device according to claim 10, comprising:
   a processing electronics block adapted to receive inputs from a fluorescence detector, to process received inputs and to provide processed information, and
   input means adapted to provide input signals to said processing electronics block;
wherein said processing electronics block is responsive to an input signal indicating the presence of an adapter in front of a front end of said measurement head by changing a processing algorithm to take into account an effect of said adapter to measurement geometry.

17. An X-ray fluorescence analyzer device according to claim 16, comprising an automatic adapter detector adapted to detect the presence of an adapter and to automatically provide said processing electronics block with said input signal indicating the presence of an adapter in front of a front end of said measurement head.

18. An X-ray fluorescence analyzer device according to claim 10, wherein an extension part of said sheet of material extends between a handle of said measurement head and the direction into which said front end is pointing.

* * * * *